US009185929B2

(12) United States Patent
Nolen et al.

(10) Patent No.: US 9,185,929 B2
(45) Date of Patent: *Nov. 17, 2015

(54) APPLICATION SYSTEM WITH RECYCLE AND RELATED USE OF ANTIMICROBIAL QUATERNARY AMMONIUM COMPOUND

(71) Applicant: SAFE FOODS CORPORATION, North Little Rock, AR (US)

(72) Inventors: Gary M. Nolen, Bella Vista, AR (US); Joe Rheingans, Rogers, AR (US); Kelly Wayne Beers, Fayetteville, AR (US)

(73) Assignee: Safe Foods Corporation, North Little Rock, AK (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,846

(22) Filed: Aug. 28, 2014

(65) Prior Publication Data

US 2014/0370172 A1 Dec. 18, 2014

Related U.S. Application Data

(63) Continuation of application No. 10/535,030, filed as application No. PCT/US03/35933 on Nov. 12, 2003, now Pat. No. 9,072,315.

(60) Provisional application No. 60/425,679, filed on Nov. 12, 2002.

(51) Int. Cl.
| | |
|---|---|
| *A61L 2/00* | (2006.01) |
| *A23F 5/00* | (2006.01) |
| *A23L 3/3454* | (2006.01) |
| *A23B 4/20* | (2006.01) |
| *A23B 4/26* | (2006.01) |
| *A23L 3/3463* | (2006.01) |

(Continued)

(52) U.S. Cl.
CPC .................. *A23L 3/3454* (2013.01); *A23B 4/20* (2013.01); *A23B 4/26* (2013.01); *A23L 3/3463* (2013.01); *A23L 3/3526* (2013.01); *A61L 2/18* (2013.01)

(58) Field of Classification Search
CPC ................................ A61L 2/18; A23L 3/3454
USPC ........................................... 422/292; 426/310
See application file for complete search history.

(56) References Cited

U.S. PATENT DOCUMENTS

RE32,695 E  *  6/1988  Nahra et al. ................... 261/118
4,965,911 A  *  10/1990  Davey .......................... 452/173

(Continued)

OTHER PUBLICATIONS

International Preliminary Examination Report, dated Sep. 25, 2005, issued by the US IPEA in Int'l Appln No. PCT/US03/35933.

*Primary Examiner* — Kevin Joyner
(74) *Attorney, Agent, or Firm* — Akerman LLP; Stephen C. Glazier

(57) ABSTRACT

An antimicrobial application system is disclosed, comprising an antimicrobial application unit and a recycle unit. An initial, dilute antimicrobial composition is prepared. The composition is provided to the antimicrobial application unit and applied to workpieces, such as raw poultry. After application to the workpieces, the composition is returned to the recycle tank. The concentration of the antimicrobial in the recycle tank is monitored, and additional antimicrobial is automatically added if the concentration of the antimicrobial in the composition falls below a desired amount. The composition is periodically diverted to a capture tank, and the antimicrobial is selectively removed from the composition. The removed antimicrobial and remaining composition are then disposed of in appropriate manners. The antimicrobial is preferably a quaternary ammonium compound, is more preferably an alkylpyridinium chloride, and is most preferably cetylpyridinium chloride.

25 Claims, 3 Drawing Sheets

(51) Int. Cl.
  *A23L 3/3526* (2006.01)
  *A61L 2/18* (2006.01)

(56) References Cited

U.S. PATENT DOCUMENTS

| | | |
|---|---|---|
| 4,996,070 A | 2/1991 | Nafisi-Movaghar |
| 5,399,541 A | 3/1995 | Ishii et al. |
| 5,421,883 A | 6/1995 | Bowden |
| 5,968,338 A | 10/1999 | Hulme et al. |
| 5,980,375 A * | 11/1999 | Anderson et al. ............... 452/77 |
| 6,126,810 A | 10/2000 | Fricker et al. |
| 2002/0064585 A1 | 5/2002 | Christianson et al. |
| 2003/0047087 A1 * | 3/2003 | Phebus et al. ................... 99/516 |

* cited by examiner ic application
APPLICATION SYSTEM WITH RECYCLE AND RELATED USE OF ANTIMICROBIAL QUATERNARY AMMONIUM COMPOUND This application is a continuation of U.S. patent application Ser. No. 10/535,030, filed Oct. 10, 2008, now U.S. Pat. No. 9,072,315, which is the 371 National Stage entry of PCT/US2003/035933, filed Nov. 11, 2003, which claims the benefit of U.S. Provisional Application Ser. No. 60/425,679, filed on Nov. 12, 2002, the disclosures of which is incorporated herein by reference in their entirety.

BACKGROUND OF THE INVENTION

This invention relates to an antimicrobial application system, and more particularly to an antimicrobial application system with recycle features for use in connection with food products and surfaces and other items associated with food processing.

Antimicrobial application systems, including spray cabinets are known in the art. U.S. patent application Ser. No. 10/001,896, filed on Nov. 19, 2002 by Gary Nolen, discusses a number of such systems and highlights a number of the advantages and disadvantages of these systems. The disclosure of U.S. patent application Ser. No. 10/001,896 (Nolen) is incorporated herein by reference. The spray application systems disclosed in that application offer a number of advantages over earlier systems, as discussed in more detail in that application. Still, the present inventors have further refined and built upon those systems to offer alternate embodiments offering additional flexibility. For example, it may be desirable to recycle the antimicrobial that is applied to the workpieces. Adding equipment and steps to allow for recycling adds to the cost and complexity of a system, so it will not always be preferred. Still, using recycling reduces consumption of the antimicrobial and water and reduces the amount of waste material in need of disposal. This may be desirable for any number of reasons such as environmental concerns, raw material costs, raw material storage limitations, disposal costs, and regulatory issues involving disposal of wastewater and some antimicrobials. Accordingly, under many circumstances, it will be desirable to recycle the antimicrobial for multiple applications to workpieces to be treated.

Recycling of liquids applied to some types of workpieces in a process line is generally known in the art. Still, recycling liquids in connection with food processing and items associated with food processing presents a number of special issues and concerns, particularly concerning adulteration, contamination, and cross-contamination. These concerns typically argue against recycling or lead to the use of slow, cumbersome, undesirable extra steps and extra equipment that add to the cost and complexity of a system. One such complex system is disclosed in U.S. Pat. No. 6,348,227, issued to Caracciolo, Jr. in 2002, the disclosure of which is incorporated herein by reference.

SUMMARY OF THE INVENTION

It is therefore an object of the present invention to provide an antimicrobial application system that provides for the safe, effective, and cost efficient recycling of antimicrobial in connection with food processing and items associated with food processing.

It is a further object of the present invention to provide a system of the above type that reduces raw material consumption without sacrificing safety.

It is a still further object of the present invention to provide a system of the above type that provides for periodic, batch style separation and disposal of spent antimicrobial.

It is a still further object of the present invention to provide a system of the above type which automatically monitors and maintains a desired composition of the antimicrobial composition to be recycled.

It is a still further object of the present invention to provide a system of the above type which provides for improved recapture and return of an antimicrobial composition applied to workpieces.

It is a still further object of the present invention to provide a system of the above type which automatically compensates for additional liquids passing from wetted workpieces to the recycled antimicrobial composition.

It is a still further object of the present invention to provide a system of the above type which is capable of providing continuous, real-time monitoring and control of the composition of an antimicrobial composition.

It is a still further object of the present invention to provide a system of the above type which reduces waste leaving the system and waste disposal costs associated therewith.

It is a still further object of the present invention to provide a system of the above type which provides a safe waste stream that may be safely drained into a wastewater system.

It is a still further object of the present invention to provide a system of the above type that increases the flexibility and advantages of the spray application systems and spray cabinets disclosed in U.S. patent application Ser. No. 10/001,896 (Nolen).

It is a still further object of the present invention to provide a system of the above type that provides a simple, reliable method of monitoring and controlling the composition of a composition to be recycled.

Toward the fulfillment of these and other objects and advantages, the antimicrobial application system of the present invention comprises an antimicrobial application unit and a recycle unit. An initial, dilute antimicrobial composition is prepared with automatically controlled concentration composition of the antimicrobial solution. The composition is provided to the antimicrobial application unit and applied to workpieces, such as raw poultry. After application to the workpieces, the composition is returned to the recycle tank of the recycle unit. The concentration of the antimicrobial in the recycle tank is monitored, and additional antimicrobial is automatically added if the concentration of the antimicrobial in the composition falls below a desired amount. The composition is periodically diverted to a capture tank, and the antimicrobial is selectively removed from the composition. The removed antimicrobial and remaining composition are then disposed of in appropriate manners. The antimicrobial is preferably a quaternary ammonium compound, is more preferably an alkylpyridinium chloride, and is most preferably cetylpyridinium chloride.

BRIEF DESCRIPTION OF THE DRAWING

The above brief description, as well as further objects, features and advantages of the present invention will be more fully appreciated by reference to the following detailed description of the presently preferred but nonetheless illustrative embodiments in accordance with the present invention when taken in conjunction with the accompanying drawing, wherein.

DETAILED DESCRIPTION OF THE PREFERRED EMBODIMENT

Figure 1:
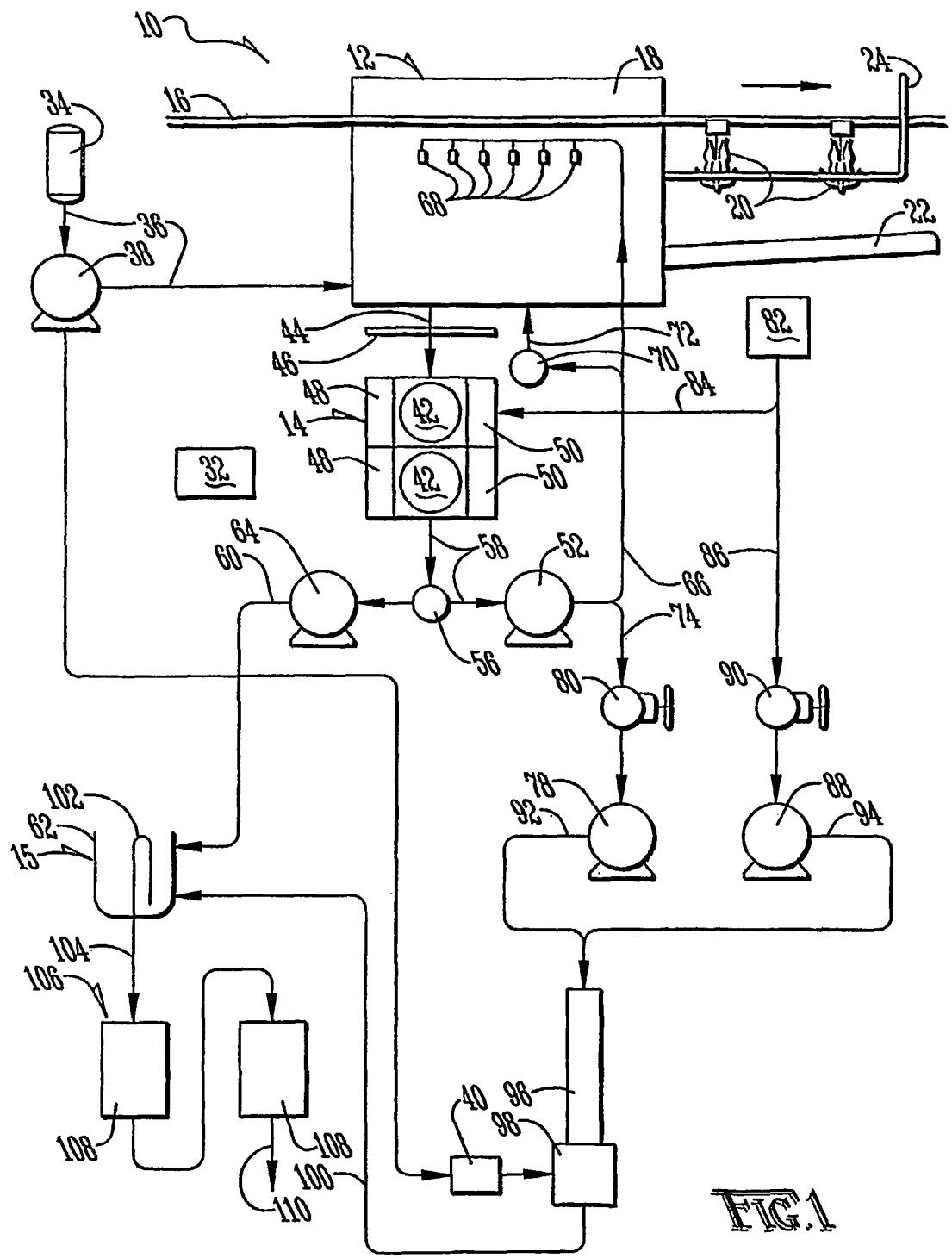
FIG. 1 is a schematic view of an antimicrobial application system of the present invention.
Figure 2:
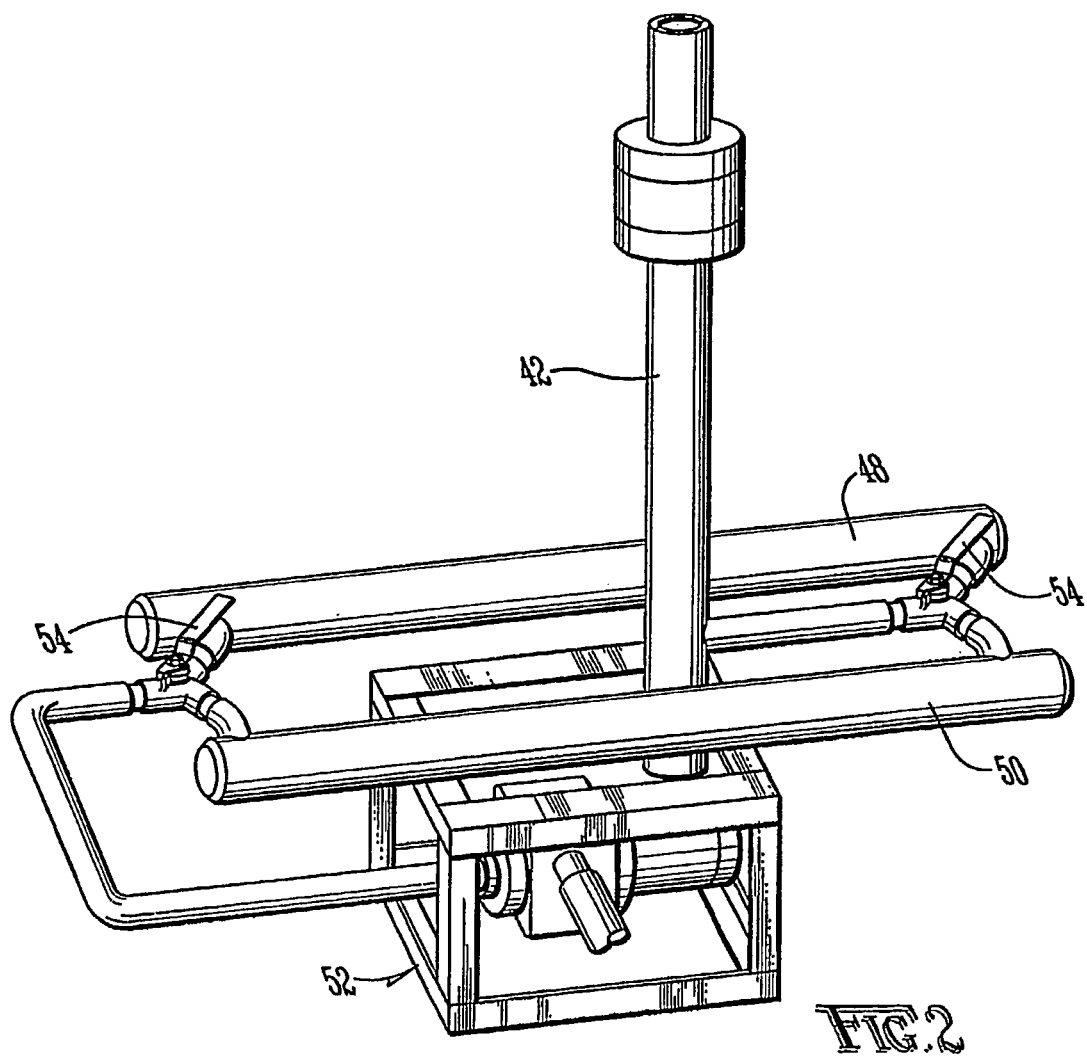
FIG. 2 is a side elevation view of a portion of a recycle unit of the present invention.

Referring to FIG. 1, the reference numeral 10 refers in general to an antimicrobial application system of the present invention. The antimicrobial application system 10 of the present invention generally comprises an antimicrobial application unit 12 and a recycle unit 14, and may include a capture unit 15.

The antimicrobial application unit 12 may take any number of configurations. In the preferred embodiment, the antimicrobial application unit 12 takes the general form of one of the embodiments of a spray application system as disclosed in U.S. patent application Ser. No. 10/001,896 (Nolen). One possible exception is that the liquid barriers described in U.S. patent application Ser. No. 10/001,896 are not used in the preferred embodiment of the present invention. A conveyor 16 passes through a housing 18 for moving workpieces 20, such as raw poultry, through the housing 18. As described in more detail below, a drip tray or pan 22 extends downstream of the housing 18, disposed below the conveyor 16 and the workpieces 20 carried thereby. Examples of spray application systems that might be used in connection with the present invention are discussed in detail in U.S. patent application Ser. No. 10/001,896 (Nolen) and will not be discussed in more detail here. It is of course understood that the antimicrobial application unit 12 is not limited to those embodiments or to spray application systems in general. The antimicrobial application unit 12 may apply a composition such as an antimicrobial composition to any number of different kinds and types of workpieces 20 in any number of different ways. Methods of application used by such an application unit 12 may include but are not limited to spraying, misting, fogging, immersing, pouring, dripping, and combinations thereof. It is understood that the system 10 may be used to treat a wide variety of different workpieces 20, including but not limited to meat, poultry, fish, fresh and salt water seafood, fruits, vegetables, other foodstuffs, animals, food packaging, and items and surfaces related to food or food processing. It is also understood that the workpieces 20 may be live, dead, raw, hide-on, carcass, pieces, cooked, prepared, processed, partially processed, ready to eat, or ready to cook. It is further understood that the system 10 may be used to treat workpieces 20 completely unrelated to food or food processing items.

Figure 3:
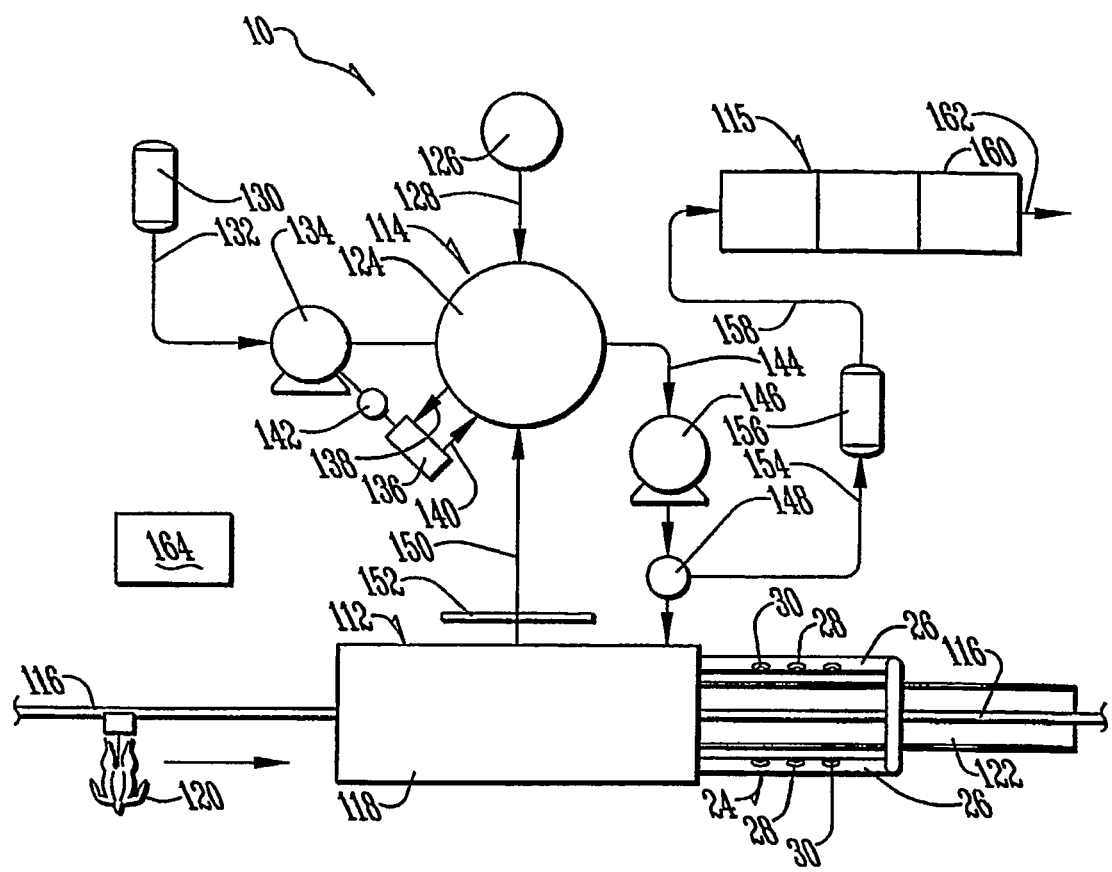
FIG. 3 is a schematic view of an alternate embodiment of an antimicrobial application system of the present invention.

A rigid member 24, such as stainless steel tubing, is affixed to the housing 18, preferably at a downstream end of the housing 18. As best seen in FIG. 3, the rigid member 24 has parallel arms 26 that are aligned on opposite sides of the conveyor line 16. A series of matching openings 28 are provided in each arm 26 for housing counters or sensors. Protective lenses 30 provide watertight seals, preferably NEMA 4 seals, to protect the counters from damage that might otherwise occur under the harsh washdown conditions to which the systems 10 are routinely subjected. Three counters are preferably provided in series. As best seen in FIG. 1, the arms 26 are disposed so that the counters are aligned to detect the presence or absence of workpieces 20. The use of three counters provides redundancy and increases accuracy. In that regard, the counters are operably connected to a controller such as a central control unit 32 or 164, and the counts taken by the three counters are continuously compared. If one counter provides a reading or count that differs from that provided by the other two, the central control unit 32 or 164 will typically be programmed to disregard the reading of the inconsistent counter and rely instead upon the readings of the other two counters. The logic and interpretation of the different readings may of course be modified in any number of ways.

The recycle unit 14 dilutes a concentrated antimicrobial composition or solution to obtain a dilute antimicrobial composition or solution and provides the dilute antimicrobial solution to the antimicrobial application unit 12. An antimicrobial source, such as a supply tank 34, is connected to the housing 18 via antimicrobial supply line or conduit 36. A chemical feed pump 38 is disposed in antimicrobial supply line 36. The pump 38 is operably connected to a controller 40 for reasons to be described below. The antimicrobial preferably comprises a quaternary ammonium compound, more preferably comprises an alkylpyridinium chloride, and most preferably comprises cetylpyridinium chloride. More particularly, the concentrated antimicrobial solution preferably comprises a concentrated solution of a quaternary ammonium compound as described in U.S. patent application Ser. No. 09/494,374, filed on Jan. 31, 2000 by Compadre et al. The disclosure of U.S. patent application Ser. No. 09/494,374 (Compadre et al.) is incorporated herein by reference. The concentrated solution preferably comprises an antimicrobial and a solubility enhancing agent, and the solubility enhancing agent preferably comprises propylene glycol. The quaternary ammonium compound is preferably present in the concentrated solution in a weight percent of approximately 40%, and the solubility enhancing agent is preferably present in the concentrated solution in a weight percent of approximately 60%. It is of course understood that any number of different antimicrobials and solubility enhancing agents may be used, and the concentrated and dilute solutions may have any number of different components and compositions, including but not limited to the components and compositions of the concentrated and dilute solutions disclosed in U.S. patent application Ser. No. 09/494,374 (Compadre et al.). Concerns of adulteration, contamination, or cross-contamination are eliminated or alleviated because of the broad-spectrum efficacy of the preferred antimicrobial solutions and because of the filtration and automatic concentration measures.

One or more recycle tanks 42 are provided. A return line or conduit 44 extends between the housing 18 and the recycle tank 42 for passing liquid from the housing 18 to the tank 42. Multiple return lines 44 may be used to connect multiple antimicrobial application units 12 to the recycle tanks 42. A filter 46 is disposed in the housing 18 or in the return line 44. The filter 46 is preferably a wire mesh filter, such as a 100 mesh filter, sized to capture visible particulate matter in the effluent from the antimicrobial application unit 12. Visible particulate matter in the effluent will typically be minimal because of upstream washing that will typically be performed on the workpieces 20. First and second filters 48 and 50 are associated with each tank 42 and are disposed between the tank 42 and a system pump 52 to provide for parallel flow between the tank 42 and the system pump 52. Valves 54 or other means are provided for selectively directing liquid passing from the tank 42 to the system pump 52 through either the first filter 48 or the second filter 50. This allows the system 10 to continue operating while one of the filters 48 or 50 is being cleaned, replaced, or repaired. A three-way valve 56 is disposed in conduit 58 for reasons to be discussed below. A purge or capture line 60 passes from the valve 56 to the capture tank 62. A capture pump 64 is disposed in capture line 60. Although the recycle tank 42 may include an impeller or some other stirring or agitation means, no such stirring or agitation means is used in the preferred embodiment. A feed line 66 passes from the system pump 52 to the housing 18 and is connected to one or more sprayers 68. Multiple feed lines 66 may be used, or the feed line 66 may be branched or divided, if desired, to connect the recycle tank 42 to multiple antimicrobial application units 12. A bypass conduit 70 having a relief valve 72 is disposed in the feed line 66. A diverting line 74 is also disposed in the feed line 66. The diverting line 74 is connected to a dilution pump 78 and has a pressure regulator 80 disposed therein.

A source of potable water 82, such as tap water, is connected to the recycle tank 42 via water supply line or conduit 84. A diverting line 86 is also disposed in water supply line 84. The diverting line 86 is connected to a dilution pump 88 and has a pressure regulator 90 disposed therein. The pressure regulators 80 and 90 preferably regulate the pressure in lines 74 and 86 to a pressure lower than the pressures in lines 66 and 84 and preferably regulate the pressure in lines 74 and 86 down to approximately 15 psig. The dilution pumps 78 and 88 are electrically interlocked to provide for matched, stroke for stroke pumping action. The dilution pumps 78 and 88 are also sized to provide for a desired, fixed dilution ratio. The dilution ratio is preferably less than or equal to approximately 1 part dilute composition to 1 part water, is more preferably less than or equal to approximately 1 part dilute composition to 30 parts water, and is most preferably less than or equal to approximately 1 part dilute composition to 60 parts water. Conduits 92 and 94 exit the dilution pumps 78 and 88 and are disposed to route liquids from the dilution pumps 78 and 88 to a static mixer 96. The static mixer is preferably an inline, auger style static mixer.

A sensor 98 is disposed at the discharge end of the static mixer 96. In the preferred embodiment, the sensor 98 is an ultraviolet light spectrophotometer or UV spec sensor. Of course it is understood that any number of different types of sensors 98 may be used, including but not limited to infrared, visible light, or ultraviolet sensors. The sensor 98 is capable of detecting the concentration of the antimicrobial in the solution exiting the static mixer 96. The controller 40 operably connects the sensor 98 to the chemical feed pump 38. The controller 40 is capable of receiving a signal from the sensor 98 and sending a corresponding on/off signal to the chemical feed pump 38. A discharge line 100 passes from the sensor 98 to the capture or purge tank 62.

A siphon 102 is disposed in the capture tank 62 and is connected to a drain line 104. The drain line 104 passes from the capture tank 62 to an antimicrobial separation unit 106. The antimicrobial separation unit 106 preferably comprises one or more filters 108, such as disposable carbon filters, that selectively remove the antimicrobial from the composition. A disposal line 110 exits the antimicrobial separation unit 106 for disposing of water and any other components remaining after the antimicrobial is selectively removed. It is understood that a separation unit 106 may or may not be used and that any number of different separation methods may be used. It is also understood that filters 108 may be disposable or reusable. The central control unit 32 is used to control the entire system 10.

In operation, a dilute antimicrobial solution will typically be prepared and used for one spray cycle that will typically last for one day. The dilute antimicrobial solution will then be discarded, disposed of, or removed from the system 10 for further processing. It is of course understood that the spray cycle may be of any number of different durations. It is also understood that the system 10 may be operated in batch mode, in steady-state mode, or in any number of different types or combinations of modes of operation. A new spray cycle will typically begin each morning with an empty and clean recycle tank 42 and an empty and clean capture tank 62. Before the antimicrobial application unit 12 is activated, and before the system pump 52 is turned on, the dilute antimicrobial solution is prepared. In that regard, a desired amount of tap water is fed to the recycle tank 42. The recycle tank 42 is preferably filled to approximately one third to approximately one half of its capacity with potable water. The concentration pump 38 is activated to feed the concentrated antimicrobial composition to the housing 18, where it drains through return conduit 44, and to the recycle tank 42, until a predetermined amount of the concentrate composition is provided. The concentrate composition combines with the water in the recycle tank 42 to form a dilute solution of the desired concentration. The desired ranges of the concentration of antimicrobial in dilute solution include but are not limited to the concentration ranges of the antimicrobial in the dilute solutions disclosed in U.S. patent application Ser. No. 09/494,374 (Compadre et al.).

Once the desired concentration is obtained in the recycle tank 42, the system pump 52 is activated, and the dilute solution is supplied to the antimicrobial application unit 12. The dilute solution provided to the antimicrobial application unit 12 is not potable. Still, contamination or cross-contamination of the workpieces 20 is not a concern because of the safety and broad spectrum efficacy of the dilute antimicrobial solution used. The recycle unit 14 supplies the dilute antimicrobial solution to the antimicrobial application unit or units 12 at any number of different flow rates and pressures. These flow rates and pressures may include, but are not limited to, the flow rates and pressures discussed in U.S. patent application Ser. No. 10/001,896 (Nolen). The bypass conduit 70 and relief valve 72 route a portion of the dilute composition to a lower portion of the housing 18 so that it does not pass through the sprayers 68 and is not applied to the workpieces 20. The ratio of dilute composition passing through the bypass conduit 70 versus passing to the sprayers 68 will typically be greater than or equal to approximately 1:1 and will more typically be greater than or equal to approximately 2:1. The dilute composition passing through the bypass conduit 70 provides for improved mixing of the captured composition and any concentrate composition that might be added. The use of the bypass conduit 70 and relief valve 72 provides greater flexibility in providing dilute composition to sprayers 68 at or within desired pressure ranges. The use of the bypass conduit 70 and relief valve 72 also makes it easier to continue to provide dilute composition to the sprayers 68 at consistent pressure as additional spray application units 12 are brought online or taken offline and regardless of the number of spray application units 12 that are online.

Once the recycle unit 14 is supplying the dilute antimicrobial solution to the antimicrobial application unit 12, the workpieces 20 to be processed, such as raw poultry, are moved by the conveyor 16, through the housing 18, and the dilute antimicrobial solution is applied to the workpieces 20, such as by spraying. The portion of the dilute antimicrobial solution that does not adhere to the workpieces 20 collects in a drain and is returned via return line 44, through filter 46, and to the recycling tank 42 for reuse. The length of the drip tray 22 is selected so that it will catch drops from workpieces 20 exiting the housing 18 for approximately 1 minute after the workpieces 20 exit the housing 18. This enhances the recovery of the dilute antimicrobial solution and reduces downstream losses. Although not preferred, liquid barriers such as water spray curtains may be used in the housing 18. Also, the workpieces 20 may be wet from upstream washing, so additional water may enter the recycle tank 42, decreasing the concentration of the antimicrobial in the dilute solution.

It is desirable to avoid concentration spikes in the dilute composition, particularly in the dilute composition exiting the sprayers 68 and passing through the diverting line 74 for routing to sensor 98. Accordingly, steps are taken to insure thorough mixing of the dilute composition being recycled between the recycle unit 14 and the antimicrobial application unit 12. This is one reason why the concentrate supply line 36 routes the concentrated antimicrobial solution to the housing 18 rather than directly to the recycle tank 42. By the time the concentrate composition mixes with dilute compositions from the sprayers 68 and from the bypass line 70, passes through return line 44, filter 44, recycle tank 42, filter 48 or 50, and system pump 52, the resultant liquid is thoroughly mixed and has a relatively uniform composition.

A preferred sensor 98, such as a spectrophotometer, is typically used to measure very low concentrations of a component in a composition. It is therefore important to provide a liquid that has not only has a relatively uniform composition but also a very low concentration of the antimicrobial or component to be measured. Often, it will not be practical or feasible to obtain accurate, reliable readings for the antimicrobial at the concentration ranges typically found in the recycle tank 42. Diluting the composition before taking a concentration reading will offer greater flexibility in the selection of a sensor 98 for monitoring the concentration of the antimicrobial. Samples of the composition exiting the recycle tank 42 are therefore taken and further diluted, to yield further diluted compositions in which the antimicrobial is present within a concentration range that is readily and accurately measured by the sensor 98. The dilution ratio of the dilution pumps 78 and 88 is selected to provide the desired degree of dilution, such as within the ranges discussed above. The pumps 78 and 88 are set on a timer to take samples at a set interval, each sample being taken for a set duration of time. It is understood that the concentration may be monitored at any number of different intervals and for any number of different durations and that the concentration may be continuously monitored. The electrically interlocked pumps 78 and 88 provide the dilute composition and water in the desired fixed ratio to further dilute the dilute composition. Using electrically interlocked pumps at a desired, fixed dilution ratio simplifies controls needed to operate the system 10. It is of course understood that the pumps need not be interlocked, the dilution ratio need not be fixed, and any number of different methods may be used to select, control, and adjust the dilution ratio as desired.

The dilute composition and water are combined and passed through the static mixer 96 to provide for thorough mixing, further reducing the risk of concentration spikes as the liquid passes the spectrophotometer 98. The spectrophotometer 98 senses the concentration of the antimicrobial in the passing liquid. The sensor 98 is operably connected to the controller 40. Accordingly, if the sensor 98 detects that the concentration of antimicrobial falls below a desired amount, the controller 40 activates the chemical feed pump 38 to add more of the concentrated antimicrobial solution into the housing 18 and to bring the concentration of the antimicrobial in the dilute antimicrobial solution back up to the desired level. The system 10 can be configured to allow the potable water to be controlled in this fashion as well, but it is unlikely that there will be a need to add make-up water.

It is undesirable to route the highly diluted liquid that passes the sensor 98 back into the recycle tank 42, so it is routed to the capture tank 62. The siphon 102 in the capture tank 62 allows the liquid to collect in the capture tank 62, until the liquid reaches a desired level. When the liquid in the capture tank 62 reaches the desired level, the siphon 102 empties the capture tank 62, passing the liquid through conduit 104 and to the disposable carbon filters 108 of the antimicrobial separation unit 106. The disposable filters 108 capture the antimicrobial to selectively remove the antimicrobial from the solution. Using the siphon 102 reduces or eliminates channeling problems that might otherwise arise if the liquid were allowed to continuously drip from the capture tank 62 onto the carbon filters 108.

At the end of the spray cycle, such as at the end of a shift or a day or other chosen period of time, the valve 56 is actuated to divert the dilute antimicrobial solution received from the recycle tank 42 to the capture pump 64. The capture pump 64 empties the recycle tank 42 and passes the dilute antimicrobial solution to the capture tank 62. When the liquid reaches a desired level in the capture tank 62, the siphon 102 routes the liquid through conduit 104 and to the disposable carbon filters 108 of the antimicrobial separation unit 106. The disposable filters 108 capture the antimicrobial to selectively remove the antimicrobial from the solution. When the antimicrobial impregnated disposable filters 108 are spent, they are then disposed of in an appropriate manner, such as by incineration or disposal at an approved landfill. The remaining, relatively antimicrobial-free liquid is then disposed of in an appropriate manner, such as by being drained into a wastewater system of a plant. The frequency with which the system 10 will need to be purged will depend upon any number of factors, such as the number of workpieces 20 to be processed by the antimicrobial application unit 12 and the volume of the dilute antimicrobial solution required to charge the system 10 at the beginning of a spray cycle. A periodic purge of the system 10 will typically be used.

An alternate embodiment of the antimicrobial application system 10 is disclosed in FIG. 3. The antimicrobial application system 10 of the alternate embodiment also generally comprises an antimicrobial application unit 112 and a recycle unit 114 and will typically include a capture unit 115.

The antimicrobial application unit 112 may take any number of configurations. For example, the antimicrobial application unit 112 may take the general form of one of the embodiments of a spray application system as disclosed in U.S. patent application Ser. No. 10/001,896 (Nolen). In the preferred embodiment, spray containment barriers are not used. A conveyor 116 passes through a housing 118 for moving workpieces 120, such as raw poultry, through the housing 118. As described in more detail below, a drip tray or pan 122 extends downstream of the housing 118, disposed below the conveyor 116 and the workpieces 120 carried thereby. The spray application systems are discussed in detail in U.S. patent application Ser. No. 10/001,896 (Nolen) and will not be discussed in more detail here. It is of course understood that the antimicrobial application unit 112 is not limited to those embodiments or to spray application systems in general. The antimicrobial application unit 112 may apply an antimicrobial to any number of different types of workpieces 120 in any number of different conventional ways. Methods of application used by such an antimicrobial application unit 112 may include but are not limited to spraying, misting, fogging, immersing, pouring, dripping, and combinations thereof. It is understood that the system 10 may be used to treat a wide variety of different workpieces 120, including but not limited to meat, poultry, fish, fruits, vegetables, other foodstuffs, animals, food packaging, and items and surfaces related to food or food processing. It is also understood that the workpieces 120 may be live, dead, raw, cooked, prepared, processed, partially processed, or ready to eat. It is also understood that the system 10 may be used to treat workpieces 120 completely unrelated to food or food processing items.

The recycle unit 114 dilutes a concentrated antimicrobial composition to obtain a dilute antimicrobial composition and provides the dilute antimicrobial composition to the antimicrobial application unit 112. A recycle tank 124 is provided. The recycle tank 124 may include an impeller or some other stirring or agitation means. A source of potable water 126, such as tap water, is connected to the recycle tank 124 via water supply line 128. Similarly, an antimicrobial source, such as a supply tank 130, is connected to the recycle tank 124 via antimicrobial supply line 132. The antimicrobial preferably comprises a quaternary ammonium compound, more preferably comprises an alkylpyridinium chloride, and most preferably comprises cetylpyridinium chloride. More particularly, the concentrated antimicrobial composition preferably comprises a concentrated composition of a quaternary ammonium compound as described in U.S. patent application Ser. No. 09/494,374, filed on Jan. 31, 2000 by Compadre et al. The disclosure of U.S. patent application Ser. No. 09/494,374 (Compadre et al.) is incorporated herein by reference. The concentrated composition preferably comprises an antimicrobial and a solubility enhancing agent, and the solubility enhancing agent preferably comprises propylene glycol. The quaternary ammonium compound is preferably present in the concentrated composition in a weight percent of approximately 40%, and the solubility enhancing agent is preferably present in the concentrated composition in a weight percent of approximately 60%. It is of course understood that any number of different antimicrobials and solubility enhancing agents may be used, and the concentrated and dilute compositions may have any number of different components and compositions, including but not limited to the components and compositions of the concentrated and dilute compositions disclosed in U.S. patent application Ser. No. 09/494,374 (Compadre et al.). Concerns of contamination or cross-contamination are eliminated or alleviated because of the broad spectrum efficacy of the preferred antimicrobial compositions.

A chemical feed pump 134 is disposed in antimicrobial supply line 132. A sensor 136 is connected to the recycle tank 124 via lines 138 and 140. In the preferred embodiment, the sensor is an ultraviolet light photospectrometer or UV spec sensor. It is of course understood that any number of different sensors and any number of different light sensors may be used. For example, the light sensor may use light having wavelengths that fall in any number of different ranges, including but not limited to ultraviolet light, visible light, infrared light, and combinations thereof. Of course it is understood that any number of different types of sensors 136 may be used, including but not limited to infrared, visible light, or ultraviolet sensors. The sensor 136 is capable of detecting the concentration of the antimicrobial in the composition in the recycle tank 124. A controller 142 operably connects the sensor 136 to the chemical feed pump 134. The controller 142 is capable of receiving a signal from the sensor 136 and sending a corresponding on/off signal to the chemical feed pump 134. A feed line 144 exits the recycle tank 124, passes through the system pump 146, through a valve 148, and connects to the antimicrobial application unit 112. Multiple feed lines may be used, or the feed line 144 may be branched or divided, if desired, to connect the recycle tank 124 to multiple antimicrobial application units. The valve 148 is preferably a three-way valve. A return line 150 exits the antimicrobial application unit 112, passes through a filter 152, and connects to the recycle tank 124. Multiple return lines may be used to connect multiple antimicrobial application units to the recycle tank 124. The filter 152 is preferably a wire mesh filter sized to capture visible particulates in the effluent from the antimicrobial application unit 112. Visible particulates in the effluent will typically be minimal because of upstream washing that will typically be performed on the workpieces 120. A capture line 154 passes from the valve 148 to a capture tank 156. A drain line 158 passes from the capture tank 156 to an antimicrobial separation unit 160. The antimicrobial separation unit 160 preferably comprises one or more disposable filters selected to separate the antimicrobial from water. A disposal line 162 exits the antimicrobial separation unit 160 for disposing of water after the antimicrobial is removed. A central control unit 164 is used to control the entire system 10.

In operation, a dilute antimicrobial composition will typically be prepared and used for one spray cycle that will typically last for one day. The dilute antimicrobial composition will then discarded, disposed of, or removed from the system 10 for further processing. Accordingly, each spray cycle, typically beginning each morning, begins with an empty and clean recycle tank 124 and an empty and clean purge or capture tank 156. Before the antimicrobial application unit 112 is activated, and before the system pump 146 is turned on, the dilute antimicrobial composition is prepared. In that regard, a desired amount of tap water is fed to the recycle tank 124. The recycle tank 124 is preferably filled to approximately one third to approximately one half of its capacity with potable water. The central control unit 164 activates the sensor 136 so that liquid from the recycle tank 124 passes through the sensor 136. The sensor 136 initially detects the absence of antimicrobial (no absorbance at 260 nm), so the controller 142 activates the chemical feed pump 134 to begin metering the concentrated antimicrobial composition into the recycle tank 124. When the concentration of the antimicrobial in the dilute composition in the recycle tank 124 reaches a desired level, the sensor 136 and, in turn, the controller 142 turn off the chemical feed pump 134. The desired ranges of the concentration of antimicrobial in dilute composition include but are not limited to the concentration ranges of the antimicrobial in the dilute compositions disclosed in U.S. patent application Ser. No. 09/494,374 (Compadre et al.). Once the desired concentration is obtained in the recycle tank 124, the system pump 146 is activated, and the dilute composition is supplied to the antimicrobial application unit 112. The dilute composition provided to the antimicrobial application unit 112 is not potable. Still, contamination or cross-contamination of the workpieces 120 is not a concern because of the safety and broad spectrum efficacy of the dilute antimicrobial composition used. The recycle unit 114 supplies the dilute antimicrobial composition to the antimicrobial application unit or units 112 at any number of different flow rates and pressures. These flow rates and pressures may include, but are not limited to, the flow rates and pressures discussed in U.S. patent application Ser. No. 10/001,896 (Nolen).

Once the recycle unit 114 is supplying the dilute antimicrobial composition to the antimicrobial application unit 112, the workpieces 120 to be processed, such as raw poultry, are moved by the conveyor 116, through the housing 118, and the dilute antimicrobial composition is applied to the workpieces 120, such as by spraying. The portion of the dilute antimicrobial composition that does not adhere to the workpieces 120 collects in a drain and is returned via return line 150, through filter 152, and to the recycling tank for reuse. The length of the drip tray 122 is selected so that it will catch drops from workpieces 120 exiting the housing 118 for approximately 1 minute after the workpieces 120 exit the housing 118. This enhances the recovery of the dilute antimicrobial composition and reduces downstream losses. Water spray curtains may be used in the application chamber, and the workpieces 120 may be wet from upstream washing, so additional water will typically enter the recycle tank 124.

The sensor 136 continuously monitors the concentration of the antimicrobial in composition in the recycling tank. If the concentration falls below a desired amount, the sensor 136 activates the chemical feed pump 134 to add more of the concentrated antimicrobial composition and to bring the concentration of the antimicrobial in the dilute antimicrobial composition back up to the desired level. The system 10 can be configured to allow the tap water to be controlled in this fashion as well, but it is unlikely that there will be a need to add water. The dilute antimicrobial composition is thereby used repeatedly to treat any number of units of the workpieces 120 being processed.

At the end of the spray cycle, such as at the end of a shift or a day or other chosen period of time, the valve 148 is actuated to divert the dilute antimicrobial composition received from the system pump 146 through capture line 154 to the purge tank 156. The liquid in the purge tank 156 is gravity fed through the drain line 158 to the disposable filters of the antimicrobial separation unit 160. The disposable filters capture the antimicrobial to separate the antimicrobial from the composition. The antimicrobial impregnated filters are then disposed of in an appropriate manner, such as by incineration or disposal at an approved landfill. The remaining, relatively antimicrobial-free liquid is then disposed of in an appropriate manner, such as by being drained into a wastewater system of a plant. The frequency with which the system 10 will need to be purged will depend upon any number of factors, such as the number of workpieces 120 to be processed by the antimicrobial application unit 112 and the volume of the dilute antimicrobial composition required to charge the system 10 at the beginning of a spray cycle. A periodic purge of the system 10 will be used.

Other modifications, changes and substitutions are intended in the foregoing, and in some instances, some features of the invention will be employed without a corresponding use of other features. For example, the different features of the alternate embodiments may be merged or combined in any number of different combinations. Also, the antimicrobial application unit 12 may take any number of forms, shapes, and sizes and need not be one of the spray cabinet embodiments disclosed in U.S. patent application Ser. No. 10/001,896 (Nolen). Similarly, any number of different compositions may be used in any number of different concentrations, and the compositions may or may not include one or more antimicrobials. Further, any number of different separation techniques may be used in the antimicrobial separation unit 106, and the antimicrobial separation unit 106 may be used with or without a corresponding use of a capture tank 62. Further still, additional pumps, filters, and similar components may be incorporated into the system 10. Also, any number of different methods may be used to monitor the composition of the composition in the recycle tank 24. Similarly, the composition may be monitored constantly or at desired intervals. Further still, the drip tray 22 may not be used and may be any number of different lengths. Of course, quantitative information is included by way of example only and is not intended as a limitation as to the scope of the invention. Accordingly, it is appropriate that the invention be construed broadly and in a manner consistent with the scope of the invention disclosed.

What is claimed:

1. An antimicrobial application system, the system comprising:
    an application unit comprising
        a housing,
        a conveyor extending through the housing, wherein the conveyer is configured to convey workpieces through the housing,
        a sprayer positioned adjacent to the conveyor, wherein the sprayer is configured to direct a first volume of a dilute antimicrobial solution onto the workpieces conveyed through the housing on the conveyor,
        a drain positioned along a lower portion of the housing,
        a collector positioned below the conveyor and having a surface angled toward the drain, wherein the collector is configured to collect a portion of the first volume of the dilute antimicrobial solution that does not adhere to the workpieces and direct the collected portion of the first volume along the lower portion of the housing toward the drain, and
        a bypass port positioned in the housing, wherein the bypass port is configured to pass a second volume of the dilute antimicrobial solution into the lower portion of the housing to mix with the collected portion of the first volume of the dilute antimicrobial solution;
    a recycle unit comprising
        at least one recycle tank having an inlet and an outlet, wherein the inlet is fluidically coupled to the drain and configured to route the dilute antimicrobial solution from the lower portion of the housing to the recycle tank,
        a feed line operatively coupled to a pump configured to transport the dilute antimicrobial solution from the recycle tank to both the sprayer and the bypass port, and
        an orifice plate positioned in the feed line, the orifice plate configured to provide flexibility in maintaining a consistent pressure range of the first volume of dilute antimicrobial solution supplied to the sprayer; and
    a diverting line coupled to the feed line, wherein the diverting line is configured to withdraw a sample of the dilute antimicrobial solution from the feed line for transport and further dilution in a mixer, and wherein a sensor is configured to measure the concentration of the antimicrobial in the dilute antimicrobial solution from the diluted sample of the dilute antimicrobial solution.

2. The antimicrobial application system of claim 1, wherein the ratio of the second volume of dilute antimicrobial solution passing into the housing through the bypass port and the first volume of dilute antimicrobial solution directed from the sprayer is greater than or equal to about 1:1.

3. The antimicrobial application system of claim 2, wherein the ratio of the second volume of dilute antimicrobial solution passing into the housing through the bypass port and the first volume of dilute antimicrobial solution directed from the sprayer is greater than or equal to about 2:1.

4. The antimicrobial application system of claim 1, wherein the sensor comprises a UV spectrophotometer.

5. The antimicrobial application system of claim 1, further comprising a controller operatively coupled to the sensor and configured to activate addition of concentrated antimicrobial to the dilute antimicrobial solution when the concentration of antimicrobial falls below a desired value.

6. The antimicrobial application system of claim 5, further comprising an antimicrobial supply line configured to be coupled between the housing and an antimicrobial source containing a concentrated supply of quaternary ammonium compound, and wherein, when the controller activates the addition of concentrated antimicrobial to the dilute antimicrobial solution, concentrated quaternary ammonium compound is withdrawn from the antimicrobial source and supplied via the antimicrobial supply line to the lower portion of the housing to mix with the dilute antimicrobial solution therein.

7. The antimicrobial application system of claim 6, further comprising a separation unit configured to selectively separate the quaternary ammonium compound from the dilute antimicrobial solution.

8. The antimicrobial application system of claim 7, wherein the separation unit comprises two or more disposable carbon filters positioned in series downstream of a capture tank.

9. An apparatus for applying a dilute antimicrobial solution to workpieces of raw poultry, the apparatus comprising:
   a housing having an upper housing portion and a lower housing portion;
   a conveyer extending through the upper housing portion, wherein the conveyer is configured to convey a plurality of workpieces therethrough;
   a sprayer having a plurality of spray nozzles, wherein the spray nozzles are configured to direct a first volume of a dilute antimicrobial solution onto workpieces conveyed through the upper housing portion;
   a lower housing portion, wherein the lower housing portion is configured to collect a portion of the first volume of the dilute antimicrobial solution that does not adhere to the workpieces;
   a bypass port, wherein the bypass port is configured to pass a second volume of dilute antimicrobial solution into the lower housing portion to mix with the portion of the first volume of dilute antimicrobial solution collected therein;
   a drain disposed along the lower housing portion;
   at least one recycle tank having an inlet and an outlet;
   a return line extending between the drain and the inlet;
   a feed line defining a fluid path and extending between the outlet and the housing, wherein the feed line is configured to operatively couple to a pump for transporting dilute antimicrobial solution from the outlet to the housing, and wherein the feed line comprises:
      an upstream portion coupled to the outlet and defining an upstream segment of the fluid path dimensioned for transporting the dilute antimicrobial solution,
      a first downstream portion coupled to the sprayer and defining a first downstream segment of the fluid path dimensioned for transporting the first portion of the dilute antimicrobial solution,
      a second downstream portion coupled to the bypass port and defining a second downstream segment of the fluid path dimensioned for transporting the second portion of the dilute antimicrobial solution; and
   a diverting line coupled to the upstream portion of the feed line, wherein a pressure regulator is positioned in the diverting line and is configured to regulate pressure in the diverting line to a pressure lower than the pressure in the feed line, and wherein the diverting line is configured divert a sample of the dilute antimicrobial solution from the feed line for further dilution in a mixer and measurement of a concentration of antimicrobial in the dilute antimicrobial solution using a sensor.

10. The apparatus of claim 9, wherein an orifice plate is disposed in the second downstream segment of the fluid path to provide flexibility in maintaining a pressure range of the first volume of dilute antimicrobial solution supplied to the sprayer.

11. The apparatus of claim 9, wherein the ratio of the second volume of dilute antimicrobial solution passing into the housing through the bypass port and the first volume of dilute antimicrobial solution directed from the sprayer is greater than or equal to about 2:1.

12. The apparatus of claim 9, further comprising a controller operatively coupled to the sensor and configured to activate an addition of a concentrated supply of antimicrobial to the dilute antimicrobial solution when the concentration of antimicrobial falls below a desired value, and wherein, when the controller activates the addition of the concentrated supply of antimicrobial to the dilute antimicrobial solution, a concentrated supply of a quaternary ammonium compound is added to the lower housing portion of the housing to mix with the dilute antimicrobial solution therein.

13. An apparatus for applying a dilute antimicrobial solution to workpieces of raw poultry, the apparatus comprising:
   a housing having a passage configured to receive a conveyer for moving workpieces through the housing;
   a sprayer positioned at least partially in the passage, wherein the sprayer is configured to direct a first volume of a dilute antimicrobial solution onto workpieces conveyed through the housing, and wherein the housing includes a lower housing portion configured to collect a portion of the first volume of the dilute antimicrobial solution that does not adhere to the workpieces;
   a bypass port positioned in the housing, wherein the bypass port is configured to pass a second volume of dilute antimicrobial solution into the lower housing portion without passage through the sprayer to mix with the portion of the first volume of dilute antimicrobial solution collected therein;
   a drain disposed along the lower housing portion, wherein the drain is configured to drain the diluted antimicrobial solution from the lower housing portion for passage into at least one recycle tank;
   a feed line extending between the recycle tank and the housing, wherein the feed line is configured to operatively couple to a pump for transporting the dilute antimicrobial solution therethrough from the recycle tank to the housing, and wherein the feed line comprises
      a supply segment coupled to an outlet of the recycle tank and configured to pass the dilute antimicrobial solution from the recycle tank toward the housing,
      an application segment extending between the supply segment and the sprayer and configured to pass the first volume of dilute antimicrobial solution to the housing, and
      a bypass segment extending between the supply segment and the bypass port and configured to pass the second volume of antimicrobial solution to the housing; and
   a separation unit configured to selectively separate an antimicrobial component of the dilute antimicrobial solution, wherein the antimicrobial component comprises a quaternary ammonium compound.

14. The apparatus of claim 13, wherein an orifice plate is positioned in the bypass segment to provide flexibility in maintaining a consistent pressure range of the first volume of dilute antimicrobial solution supplied to the sprayer.

15. The apparatus of claim 14, wherein the ratio of the second volume of dilute antimicrobial solution passing into the housing through the bypass port and the first volume of dilute antimicrobial solution directed from the sprayer is greater than or equal to about 2:1.

16. The apparatus of claim 13, further comprising a controller operatively coupled to a sensor configured to measure a concentration of the antimicrobial in the dilute antimicrobial solution, wherein, when the concentration of the antimicrobial component in the dilute antimicrobial solution falls below a desired value, the controller is configured to activate addition of a concentrated supply of the antimicrobial component to the lower housing portion to mix with the dilute antimicrobial solution therein.

17. The apparatus of claim 13, wherein the separation unit comprises two or more disposable carbon filters positioned in series downstream of a capture tank.

18. An antimicrobial application system, the system comprising:
 an application unit comprising
  a sprayer configured to direct a first volume of a dilute antimicrobial solution onto a workpiece,
  a collector configured to collect a portion of the first volume of the dilute antimicrobial solution that does not adhere to the workpiece, and
  a bypass port configured to pass a second volume of the dilute antimicrobial solution into the application unit to mix with the collected portion of the first volume of the dilute antimicrobial solution;
 a recycle unit comprising
  an inlet to receive the mixed first and second volumes from the application unit, and
  a feed line operatively coupled to a pump configured to transport the dilute antimicrobial solution from the recycle tank to both the sprayer and the bypass port;
 an orifice plate positioned in the feed line, wherein the orifice plate is configured to provide flexibility in maintaining a consistent pressure range of the first volume of dilute antimicrobial solution supplied to the sprayer; and
 a diverting line coupled to the feed line, wherein the diverting line is configured to withdraw a sample of the dilute antimicrobial solution from the feed line for transport and further dilution in a mixer, and wherein a sensor is configured to measure the concentration of the antimicrobial in the dilute antimicrobial solution from the diluted sample of the dilute antimicrobial solution.

19. The antimicrobial application system of claim 18, wherein the ratio of the second volume of dilute antimicrobial solution passing into the application unit through the bypass port and the first volume of dilute antimicrobial solution directed from the sprayer is greater than or equal to about 2:1.

20. The antimicrobial application system of claim 18, further comprising a controller operatively coupled to the sensor and configured to activate addition of concentrated antimicrobial to the dilute antimicrobial solution when the concentration of the antimicrobial falls below a desired value.

21. The antimicrobial application system of claim 20, further comprising an antimicrobial supply line configured to be coupled between the application unit and an antimicrobial source containing a concentrated supply of quaternary ammonium compound, and wherein, when the controller activates the addition of the concentrated antimicrobial to the dilute antimicrobial solution, concentrated quaternary ammonium compound is withdrawn from the concentrated supply of quaternary ammonium compound of the antimicrobial source and supplied via the antimicrobial supply line to the application unit to mix with the first and second volumes of dilute antimicrobial solution.

22. The antimicrobial application system of claim 21, further comprising a separation unit configured to selectively separate the quaternary ammonium compound from the dilute antimicrobial solution.

23. The antimicrobial application system of claim 22, wherein the separation unit comprises two or more disposable carbon filters positioned in series downstream of a capture tank.

24. The antimicrobial application system of claim 18, wherein the workpiece comprises raw meat.

25. The antimicrobial application system of claim 24, wherein the workpiece comprises raw poultry.

\* \* \* \* \*